US006214577B1

(12) United States Patent
Yocum

(10) Patent No.: US 6,214,577 B1
(45) Date of Patent: Apr. 10, 2001

(54) YEAST VECTORS CONFERRING ANTIBIOTIC RESISTANCE

(76) Inventor: Robert Rogers Yocum, Four Orchard La., Lexington, MA (US) 02420

( * ) Notice: Subject to any disclaimer, the term of this patent is extended or adjusted under 35 U.S.C. 154(b) by 0 days.

(21) Appl. No.: 08/466,460

(22) Filed: Jun. 6, 1995

Related U.S. Application Data

(63) Continuation of application No. 07/471,673, filed on Jan. 24, 1990, now Pat. No. 5,422,267, which is a continuation of application No. 06/864,785, filed on May 19, 1986, now abandoned, which is a continuation-in-part of application No. 06/736,450, filed on May 21, 1985, now abandoned, which is a continuation-in-part of application No. 06/612, 796, filed on May 22, 1984, now abandoned.

(51) Int. Cl.⁷ .............................. C12Q 1/68; C12N 15/81; C12N 15/31; C12N 1/19
(52) U.S. Cl. .................. 435/69.1; 435/254.2; 435/320.1; 435/477; 435/483; 536/23.7; 536/23.74
(58) Field of Search ..................... 435/69.1, 171, 435/172.1, 254.21, 320.1, 254.2, 477, 483; 536/23.7, 24.1, 23.1, 23.74; 935/28, 56, 69

(56) References Cited

U.S. PATENT DOCUMENTS 4,626,505 12/1986 Falco .
4,727,028 2/1988 Santerre et al. .

FOREIGN PATENT DOCUMENTS 0068740 5/1983 (EP) .
0096430 12/1983 (EP) .

OTHER PUBLICATIONS

Kaster et al. Hygromycin B resistance as dominant selectable marker in yeast. Current Genetics vol. 8 pp. 353–358, 1984.*
Hadfield et al. G418–resistance as a dominant marker and reporter for gene expression in *Saccharomyces cerevisiae*. Current Genetics vol. 18 pp. 303–313, 1990.*

Broach et al. Transformation in yeast: Development of a hybrid cloning vector and isolation of the CAN1 gene. Gene vol. 8 pp. 121–133, 1979.*
St John et al. Deletion analysis of the Saccharomyces GAL gene cluster. Transcription from three promoters. J. Molecular Biology vol. 152 pp. 317–334, 1981.*
Fried et al., "Cloning of Yeast Gene for Trichodermin Resistance and Ribosomal Protein L3," Proc. Natl. Acad. Sci. USA 78(1):238–242, 1981.
Miyajima et al., "Expression of Plasmid R388–Encoded Type II Dihydrofolate Reductase as a Dominant Selective Marker in *Saccharomyces cerevisiae*," Mol. Cell. Biol. 4(3):407–414, 1984.
Reipen et al., "Non–Selective Transformation of *Saccharomyces cerevisiae*," Current Genetics 6:1890–193, 1982.
Rine et al., "Targeted Selection of Recombinant Clones Through Gene Dosage Effects," Proc. Natl. Acad. Sci. USA 80:6750–6754, 1983.
Fogel et al. Tandem gene amplification mediates copper resistance in yeast. Proc. Natl. Acad. Sci. USA vol. 79 pp. 5342–5346, 1982.*
Gritz et al. Plasmid–encoded hygromycin B resistance: the sequence of Hygromycin B phosphotransferase gene and its expression in *Escherichia coli* and *Saccharomyces cerevisiae*. Gene vol. 25 pp. 179–188, 1983.*
Davies, Julian et al., American Journal of Tropical Medicine and Hygiene, vol. 29, No. 5 (1980), (PP. 1089–1092).
Webster, Thomas D. et al., Gene, vol. 26, Dec/83 (PP. 243–252).
Lawyer et al., The Molecular Biology of Yeast: Derivation and Use of a Dominant Selectable Marker for Yeast, p.190, Cold Spring Harbor, New York, Aug/16–Aug/21, 1983.

* cited by examiner

*Primary Examiner*—John S. Brusca
(74) *Attorney, Agent, or Firm*—Clark & Elbing LLP

(57) ABSTRACT

A vector having a gene for resistance to an antibiotic otherwise capable of killing a host yeast cell, the gene being transcribed from a yeast promoter sequence.

12 Claims, 7 Drawing Sheets

5'-AATTCTACTCGCCCTGAGCGGCCTCGTCTGCACAGGGTTGGCAAATGTGATTTCCAAG
GATGAGCGGGACTCGCCGGAGCAGACGTGTCCCAACCGTTTACACTAAAGGTTCGCGC-5'

YEAST VECTORS CONFERRING ANTIBIOTIC RESISTANCE

CROSS REFERENCE TO RELATED APPLICATIONS

This application is a continuation of pending prior application Ser. No. 07/471,673 filed on Jan. 24, 1990, now U.S. Pat. No. 5,422,267 issued Jun. 6, 1995, which is a continuation of application Ser. No. 06/864,785 filed on May 19, 1986, now abandoned, which is a continuation-in-part of application Ser. No. 06/736,450 filed on May 21, 1985, now abandoned, which is a continuation-in-part of application Ser. No. 06/612,796 filed on May 22, 1984, now abandoned, all of which are hereby incorporated by reference.

BACKGROUND OF THE INVENTION

This invention relates to the genetic engineering of cells and to beer brewing.

Technology currently exists for introducing heterologous (i.e., modified or foreign) genes into laboratory strains of yeast of the genus Saccharomyces, particularly *S. cerevisiae*. Two types of plasmid vectors have been used for this purpose, replicating and integrating. Replicating vectors contain an origin of DNA replication that functions in yeast, so that the plasmid is maintained extrachromosomally, as a circular episome. Integrating vectors do not contain such an origin and therefore require insertion into a yeast chromosome to be stably maintained.

Both types of plasmids can be introduced into yeast cells by standard transformation methods. Since successful uptake and establishment of plasmid DNA by competent yeast cells is a relatively rare event ($<10^{-3}$), a selection mechanism is required to allow identification of transformants.

Most commonly, selection is accomplished by introducing auxotrophic mutations into the recipient yeast strain. The commonly used mutations are ura3, leu2, trp1, and his3. The plasmid of interest bears a wild type copy of one of these genes. Since the wild type copy on the plasmid is dominant to the host chromosomal allele, selection for cells that receive the plasmid is easily accomplished on a minimal medium lacking the nutrient that is required by the auxotrophic host cell.

There have also been reports of the use of antibiotic resistance to select transformed cells. Replicating vectors have been described that are based on the sensitivity of most Saccharomyces strains to the commercially available neomycin analog, antibiotic G418. Jimenez et al. (1980) Nature 287, 869; Hollenberg (1982) In *Current Topics in Microbiology and Immunology*, Hofschneider et al., eds. (Springer-Verlag NY); Webster et al. (1983) Gene 26, 243. Webster et al. also describe an integrating plasmid vector which could not be directly selected for by resistance to G418. These vectors contain a gene, called kan$^r$, neo$^r$, or G418$^r$ from the bacterial transposon Tn903, and a yeast origin of replication; the bacterial gene is preceded by its native bacterial promoter.

Another replicating vector has been described which contains the gene for resistance to the antibiotic hygromycin B under the control of a yeast promoter. Gritz et al. (1983) Gene 25, 178.

Beer brewing using yeasts, e.g., members of the genus Saccharomyces, requires the presence of mono-, di-, or tri-saccharides in the fermentation culture medium ("wort"), which the yeasts metabolize in the production of ethanol, $CO_2$ and other metabolites. After yeast fermentation, starches and complex oligosaccharides (those larger than three glucose units) remain soluble but unmetabolized. These oligosaccharides, which are flavorless and colorless, add only to the caloric content of beer.

The production of low starch ("light") beer requires removal of some of the unmetabolized soluble starch and complex oligosaccharides present in the wort that normally remain in the beer after fermentation by yeast. Several methods have been used to reduce the content of starch and complex oligosaccharides in low calorie beer:

1) Passing the wort over an immobilized enzyme, glucoamylase, which is capable of breaking down starch and complex oligosaccharides.

2) Addition of soluble glucoamylase to the wort prior to or during fermentation.

3) Prolonging the mashing process, during which endogenous barley amylases degrade starch.

4) Adding malt flour to the wort during fermentation.

5) Substituting fermentable sugars, such as corn syrup, for various amounts of the starch derived from cereal grains.

6) Diluting the final product with water.

SUMMARY OF THE INVENTION

The invention features a vector including a gene for resistance to an antibiotic otherwise capable of killing a host yeast cell, the gene being transcribed from a yeast promoter sequence or synthetic promoter sequence, the vector being capable of being directly selected for.

A gene heterologous to the host yeast cell (i.e., a non-yeast gene, a modified gene, a gene from a different yeast strain, or a homologous gene from a different chromosomal location) can be inserted into the vector, and the vector used to transform the host cells; transformants are selected on the basis of antibiotic resistance.

In a preferred embodiment, the invention features a replicating vector which includes a gene for resistance to G418, which gene is under the control of a yeast control sequence.

In other preferred embodiments, the heterologous gene encodes an enzyme, e.g., glucoamylase (which enables the generation of glucose from starch by the yeast cell), and the host cell participates in a process, e.g., the production of dough, which employs a product of the metabolism of the cell.

In other preferred embodiments, the antibiotic resistance gene and the heterologous gene are under the control of different promoters, the promoter controlling the heterologous gene preferably being the more highly expressed of the two.

Introduction of genes encoding heterologous enzymes into industrial yeast strains using the vectors of the invention will facilitate the production of such products as alcohol, which ordinarily relies on sugars to feed the yeast. An enzyme such as glucoamylase will enable the yeast to break down starch from inexpensive sources such as tapioca and potatoes to yield glucose, which can be fed on by the yeast. Similarly, bread-making can be made cheaper when starch (flour) rather than sugar is used as the primary energy source.

In another aspect, the invention features a diploid or greater ploidy yeast cell transformed with DNA encoding glucoamylase, the yeast cell being capable of producing enzymatically active glucoamylase.

In preferred embodiments, the yeast cell is diploid, triploid, tetraploid, or aneuploid; the glucoamylase-encoding DNA is introduced via a plasmid capable of integrating into a chromosome of the host yeast cell via a sequence on the plasmid homologous with a region of a chromosome of the host cell; the plasmid is integrated into more than one such homologous region-containing chromosome in the host cell; the glucoamylase-encoding DNA is substantially identical to glucoamylase coding sequences of DNA of the mold *Aspergillus niger;* and the host yeast cell is a beer brewing strain (most preferably lager) used to brew beer, (e.g., light beer) or is a spirits (e.g.;, whiskey or fuel ethanol) distilling or bread-making strain.

The plasmids of the intention can be integrated in a way which results in the plasmid DNA remaining substantially intact in the host chromosome, or in a way which results in the jettisoning of unwanted plasmid sequences, e.g., *E. coli* sequences. In both cases, the plasmid includes a region homologous with a region of the host chromosome. In the jettisonning case, the plasmid, prior to transformation, is linearized (as it is also in the non-jettisonning case), and the homologous sequence of the host chromosome has a first and a second end and the plasmid includes a first and a second sequence, respectively homologous with the first and second ends, which sequences are separated from each other by a region of partial non-homology which includes the DNA encoding glucoamylase, a third sequence homologous with the corresponding region of the host chromosome, DNA encoding a selectable trait, and DNA encoding a screenable trait.

In another aspect, the invention features an improved method of transforming diploid or greater ploidy yeast cells with plasmid DNA involving contacting the cells and the plasmid DNA under transforming conditions, plating the cells on a porous support, and then selecting transformants, the temperature of the yeast cells being maintained below 40° C. for the entire period during the transforming and selecting steps.

The invention makes possible the use of modified forms of the yeast strains normally used in brewing to degrade complex oligosaccharides to produce low-calorie light beer, obviating the addition of exogenous enzyme or diluents, or the use of additional or longer brewing steps, while preserving the distinctive flavor characteristics of the beer imparted by the brewing strain. The invention also makes possible an increased yield of distilled ethanol from the fermentation of grain or other starch-containing mashes. The invention also reduces the sugar requirement in leavening of bread by yeast.

The invention also features a DNA sequence that includes a gene for resistance to an antibiotic otherwise capable of killing a host yeast cell, the gene being transcribed from a yeast promoter sequence or a synthetic promoter sequence and being capable of being selected for in the integrated state.

Other enzymes can facilitate commercial fermentation processes in other respects. For example, in wine-making, insertion of the gene for malolactic enzyme or malate permease will permit host yeast cells to metabolize malic acid from grapes, thus inhibiting spoilage of the wine by removing malic acid, which is otherwise fed on by spoilage bacteria.

Other features and advantages of the invention will be apparent from the following description of preferred embodiments thereof, and from the claims.

DESCRIPTION OF THE PREFERRED EMBODIMENTS

The drawings will first briefly be described.

Drawings

Transformation

Figure 1:
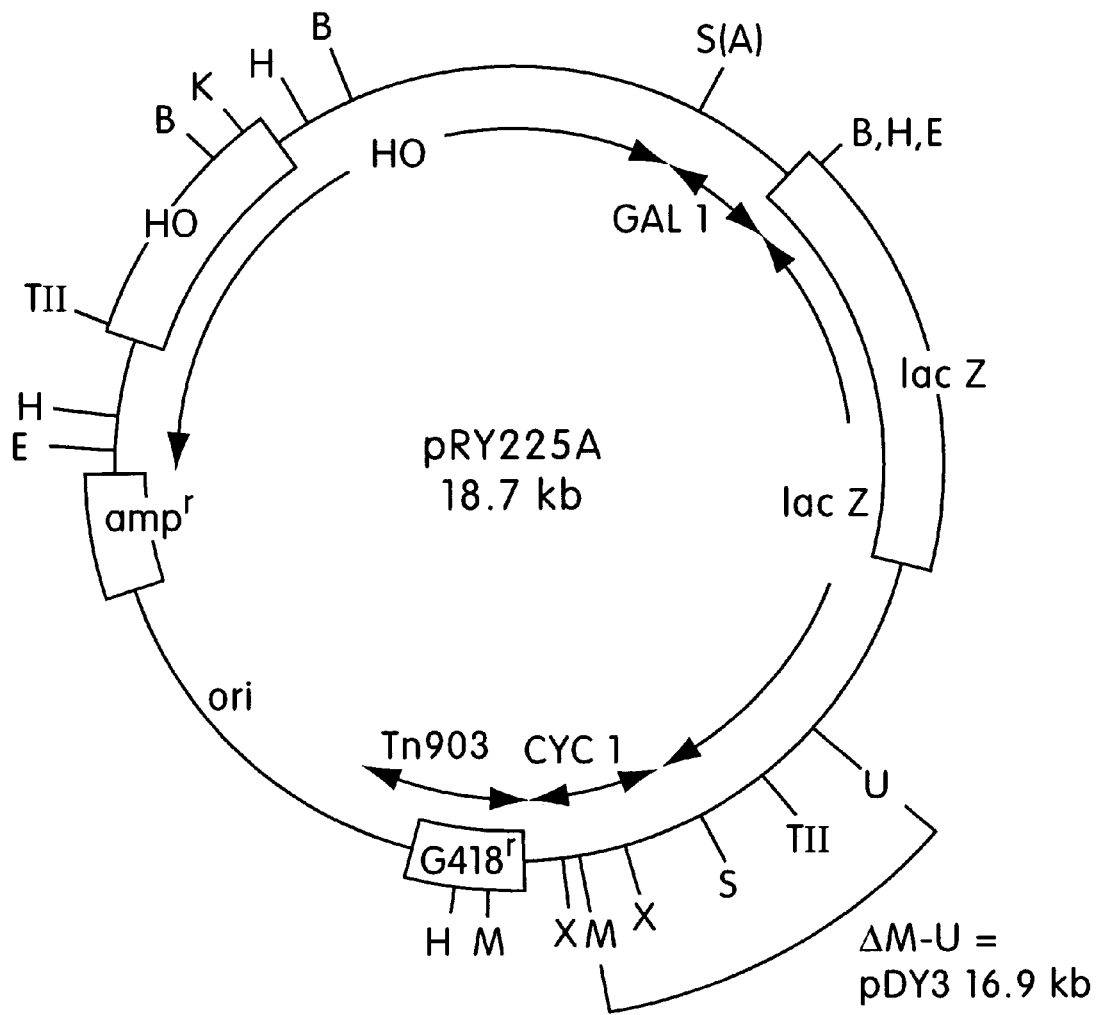
FIGS. 1 and 3 are diagrammatic representations of plasmids used in the construction of the plasmid of FIG. 2.

Transformation of host yeast cells is carried out using any suitable technique. Yeast cells were transformed with vectors of the invention as follows.

Laboratory yeast strain DBY 745 (described in Guarente et al. (1981) PNAS USA 78, 2199); a Carlsberg brewing strain (isolated from unpasteurized beer); Fleischman's$^R$ baking yeast (purchased at a supermarket); and a Bordeaux wine yeast (ATCC 42928) were grown in a standard rich medium, YEP-D, spheroplasted with glusulase, and exposed to plasmid DNA by standard methods of yeast transformation, as described in Sherman et al. (1981) *Methods in Yeast Genetics* (Cold Spring Harbor Laboratories Press, Cold Spring Harbor, N.Y.). Integrating plasmid pRY253 was linearized by restriction endonuclease digestion, at a unique SstII site near the 3' end of the HO gene, and pRY255 was linearized at a unique KpnI site near the 5' end of the HO gene, prior to transformation, in order to direct integration at the HO locus. Replicating plasmid pRY252 was not linearized.

After exposure to the plasmids, $10^8$ spheroplasts were grown in YEP-D plus 1.0M sorbitol for 30 minutes at 30° C. and then plated in 6 ml of warm 3% agarose containing YEP-D over 20 ml of 2% agar, YEP-D, 1.0M sorbitol, and 70 mM potassium phosphate, pH 7.0. After 10 minutes of cooling at room temperature, another 4 ml of warm 1% agar, YEP-D, 1.0M sorbitol was layered over the top agar. The cells were then allowed to grow at 30° C., for 6 generations, corresponding to 8 hours for DBY 745, 9 hours for Carlsberg, 7 hours for the wine yeast, and 6 hours for Fleishman's. After this "growing out" period, 0.6 ml of a sterile solution of antibiotic G418 at 25 mg/ml was spread over the agar surface and allowed to dry in a sterile hood. The plates were then incubated for 2–5 days at 30° C., after which time colonies appeared out of a background of untransformed cells. Several of these colonies were toothpicked onto fresh YEP-D plates containing 500 μg/ml G418. Cells that were successfully transformed gave rise to visible colonies within 24 hours, while untransformed cells did not. A summary of these results is given in Table 1, below.

TABLE 1

Number of G418 resistant transformants per $10^8$ competent cells from 1 μg of plasmid DNA.

| | DNA | | | |
|---|---|---|---|---|
| Strain | None | pRY252 | pRY253 | pRY255 |
| DBY 745 | 0 | 5,200 | 890 | 800 |
| Carlsberg | 0 | 260 | 13 | 7 |
| Wine Yeast (ATCC #42928) | 0 | 450 | 30 | 21 |
| Fleishman's | 0 | 510 | 22 | 17 |

Plasmid Components

As is mentioned above, plasmids of the invention useful for the transformation of yeast cells for the fermentation of starches in the production of, e.g. light beer, include several components, now discussed in more detail.

DNA Encoding Glucoamylase

The glucoamylase-encoding DNA used to transform the yeast cells of the invention can be derived from many sources; the most preferred DNA is the glucoamylase gene of the bread mold A. niger. "Glucoamylase" refers to any exo-enzyme capable of degrading glucose-containing oligosaccharides more than three units in length. As will be described in more detail below, it is not necessary that the enzyme include the entire product of the structural gene which encodes the naturally occurring enzyme; we have shown that a less than complete gene product, encoded by a less than complete structural gene, exhibits glucoamylase activity. In addition, some microorganisms produce more than one form of glucoamylase. For example, A. niger is known to produce two forms of secreted glucoamylase, called GI and GII (Boel et al. (1984) EMBO J. 3, 1097). Form GI results from the splicing out of four introns at the mRNA level; form GII results from the splicing out of the same four introns plus an addition fifth intron of 169 bases located near the 3' end of the transcript.

Regulatory DNA

In order for the glucoamylase-encoding DNA to be adequately expressed in the host yeast cells, transcription of the DNA must be under the control of a promoter sequence which is recognized by the yeast transcriptional machinery. Preferred are promoter sequences isolated from or substantially identical to yeast promoters, e.g. the promoter naturally controlling transcription of the S. cerevisiae triose phosphate isomerase ("TPI") gene.

In addition to a promoter sequence, there is preferably, downstream from the glucoamylase-encoding DNA, a suitable transcription terminator, which is also preferably derived from a yeast cell such as S. cerevisiae, and preferably, but not necessarily, derived from the same gene as the promoter used.

Integration Sequence

It is preferred that the vector of the invention be capable of integration into a chromosome of the host yeast cell. This is preferably accomplished by means of a sequence on the vector which is homologous with a sequence (a "target" sequence) of a host chromosome. Preferably, the homologous sequence is a region in which integration will not adversely affect the metabolism and flavor characteristics of the host cell. A preferred target region on the host chromosome is the homothallism (HO) gene, which is advantageously large, and is not related to flavor characteristics of the host yeast.

Integration provides stability over many host cell generations in the absence of selection, an important advantage in industrial fermentation processes and brewing; autonomously replicating plasmids can be lost from yeast cells at rates up to 1% to 5% per generation.

Selectable Marker

Because transformation of yeast cells with plasmids is a relatively rare event, vectors of the invention preferably contain a DNA region which encodes a selectable marker protein for the identification of transformants. This marker protein can be any protein which can be expressed in host yeast cells and which enables the phenotypic identification of yeast cells which express the protein. Preferred marker proteins are proteins which confer resistance to one or more antibiotics, e.g., antibiotic G418. Transformants are those cells able to grow in the presence of the antibiotic.

Host Yeast Cells

The yeast cells transformed and cultured according to the invention are diploid or greater ploidy strains used in beer and ale brewing, or in distilled spirits (e.g., whiskey) and bread making. Generally, S. cerevisiae strains, which are "top fermenting" strains, are used in making ales, while S. uvarum strains, which are "bottom fermenting" strains, are used in making lager beer, including light beer. Beer and ale brewing strains often are tetraploid, while whiskey and other distillery, and bread strains, are often diploid. Other industrial strains are aneuploid, i.e., of a ploidy not an exact multiple of haploid.

The yeast strains used in the invention are those which already are capable of metabolizing simple sugars to produce the desired ale, beer, whiskey, other distilled spirit, or bread product with the characteristic flavor of the product, and which only lack, prior to transformation according to the invention, the ability to metabolize complex oligosaccharides and starches. Many suitable yeast strains are publicly available.

As already mentioned, the invention permits the production of light beer or ale without additional steps to remove oligosaccharides. In the case of whiskey and other distilled spirits, and bread, the invention permits the use of lower-cost starting materials, i.e. starch rather than sugar, while retaining the desirable flavor characteristics of the fermenting strain.

Plasmid Structure

In the figures, the following abbreviations are used for restriction endonuclease cleavage sites: A, XbaI; B, BamHI; Bs, BssHII; E, EcoRI; H, HindIII; K, KpnI; L, BclI; M, SmaI; P, PstI; PI, PvuI; PvuII; S, SalI; Sp, SphI; T, SstII; U, StuI; X, XhoI. (A) denotes the position of a former XbaI site located about 3 kilobases upstream from the 5' end of the HO gene. This site was destroyed and replaced by a SalI site in the construction of an intermediate vector, pRY253, described in Yocum "Yeast Vector", U.S. Ser. No. 736,565, assigned to the same assignee as the present application, hereby incorporated by reference. (PII) represents a former PvuII site similarly lost. In FIG. 1, complete genes or gene fusions are shown by boxes. The abbreviations for the genes are as follows: amp$^r$, ampicillin resistance; G418$^r$, antibiotic G418 resistance; HO, homothallism; CYC1, iso-1-cytochrome c; GAL1, galactokinase; lacZ, beta-galactosidase; GA, A. niger preflucoamylase; TPI, triose phosphate isomerase. The concentric arrows inside the circles indicate segments of DNA having origins as indicated; no arrow indicates E. coli origin. Other abbreviations are: kb, kilobase pairs; ori, E. coli origin of replication.

Figure 2:
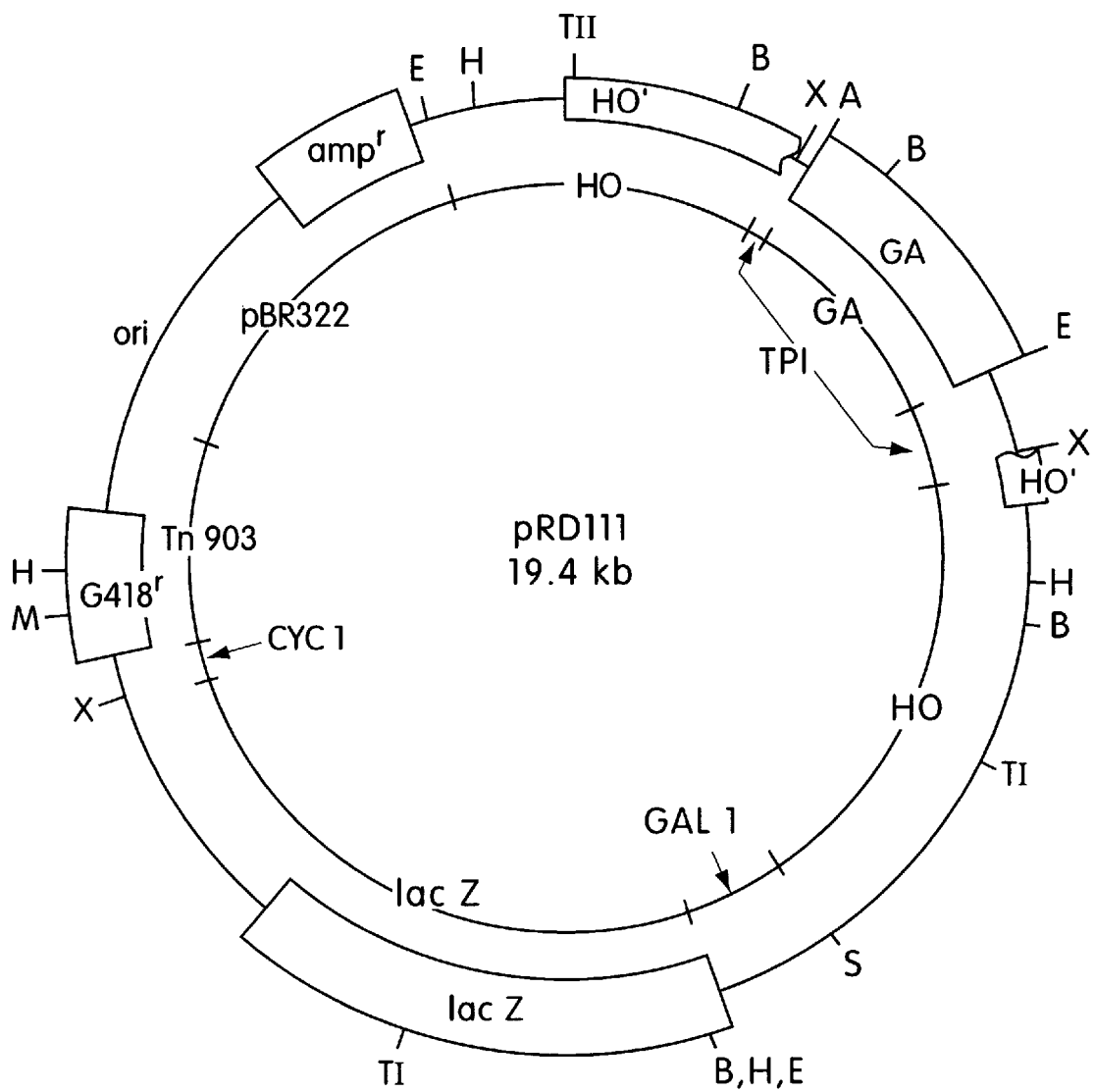
FIGS. 2 and 5 are diagrammatic representations of plasmids of the invention.

Referring to FIG. 1, plasmid pDY3, into which the A. niger preglucoamylase gene was inserted, is described in Yocum, Id. pDY3 is composed, beginning at the one o'clock position and moving clockwise, of an XhoI to StuI fragment containing a gene fusion of the yeast GAL1 gene and the E. coli lacZ gene; a SmaI to PvuII fragment including the yeast CYC1 promoter and most of the gene for resistance to the antibiotic G418 from the bacterial transposon Tn903 (the non-essential N-terminal region is not included); a PvuII to EcoRI fragment including the E. coli origin of replication from pBR322 and the amp' gene for selecting transformants in *E. coli;* and an EcoRI to XbaI fragment of *S. cerevisiae* containing the HO gene, including a KpnI site for the insertion of the *A. niger* preglucoamylase gene. FIG. 2 illustrates pRD111, which contains that gene. In FIG. 2, the source of all DNA is indicated on the inner concentric circle.

Figure 6:
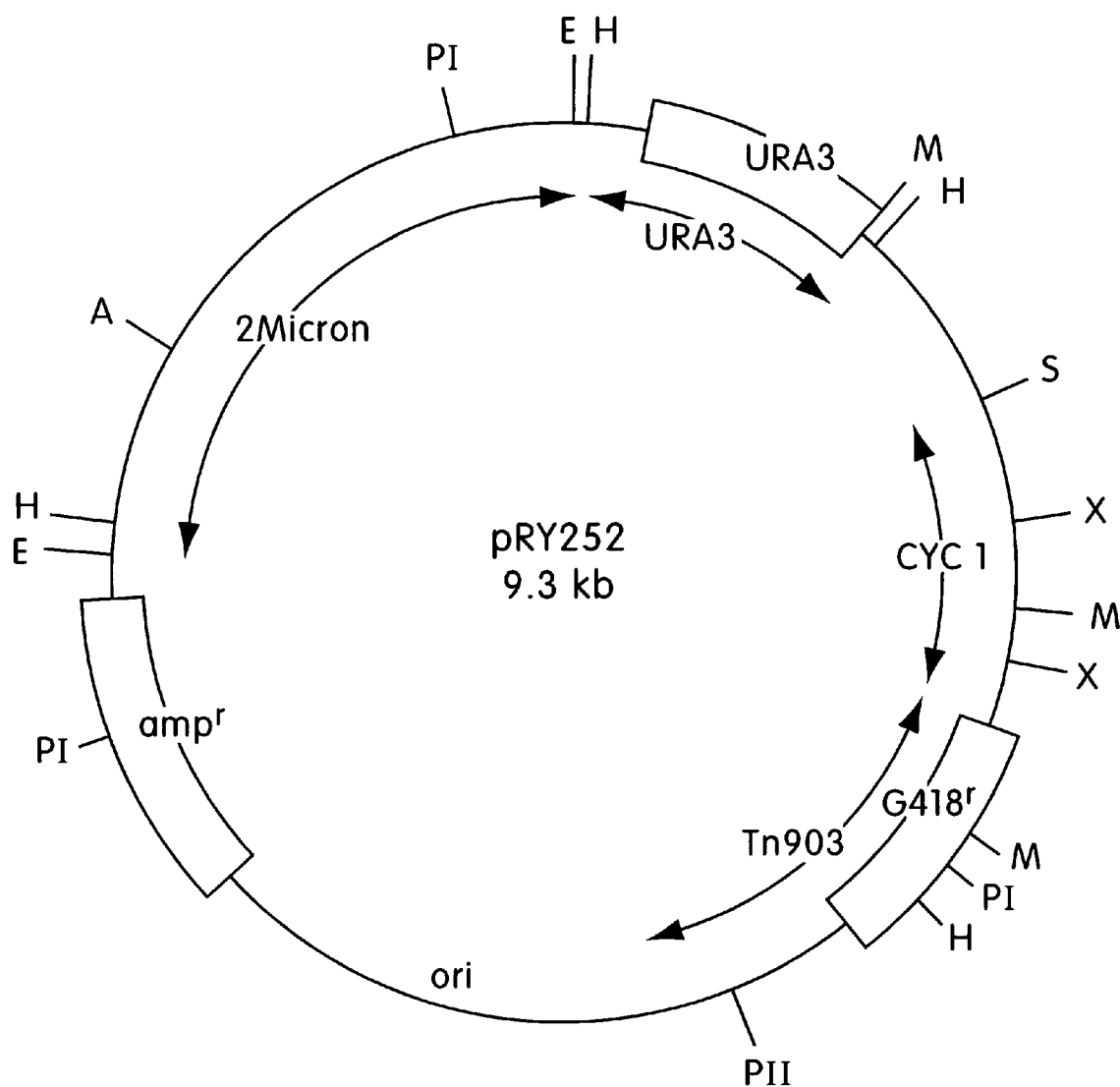
FIG. 6 is a diagrammatic representation of a replicating vector of the invention.

Referring to FIG. 6, replicating plasmid vector pRY252 is composed, beginning at the 12 o'clock position of the drawing and moving clockwise, of sequence E-H, a small piece of DNA from the *E. coli* plasmid pBR322; sequence H-H, which includes the yeast URA3 gene (one of the genes required for the ability to grow on uracil-deficient media; this gene is an unnecessary artifact in the plasmid which was originally inserted to provide a comparative selection means); sequence H-S, another piece of pBR322; sequence S-(PII), which includes the yeast CYC1 (cytochrome c) promoter and most of the gene for resistance to G418 form the bacterial transposon Tn903 (the non-essential N-terminal region is not included); sequence (PII)-E, including the *E. coli* origin of replication from pBR322 and the amp$^r$ gene for selecting transformants in *E. coli;* and sequence E-E, the yeast origin of replication from a yeast 2 micron circle.

Figure 7:
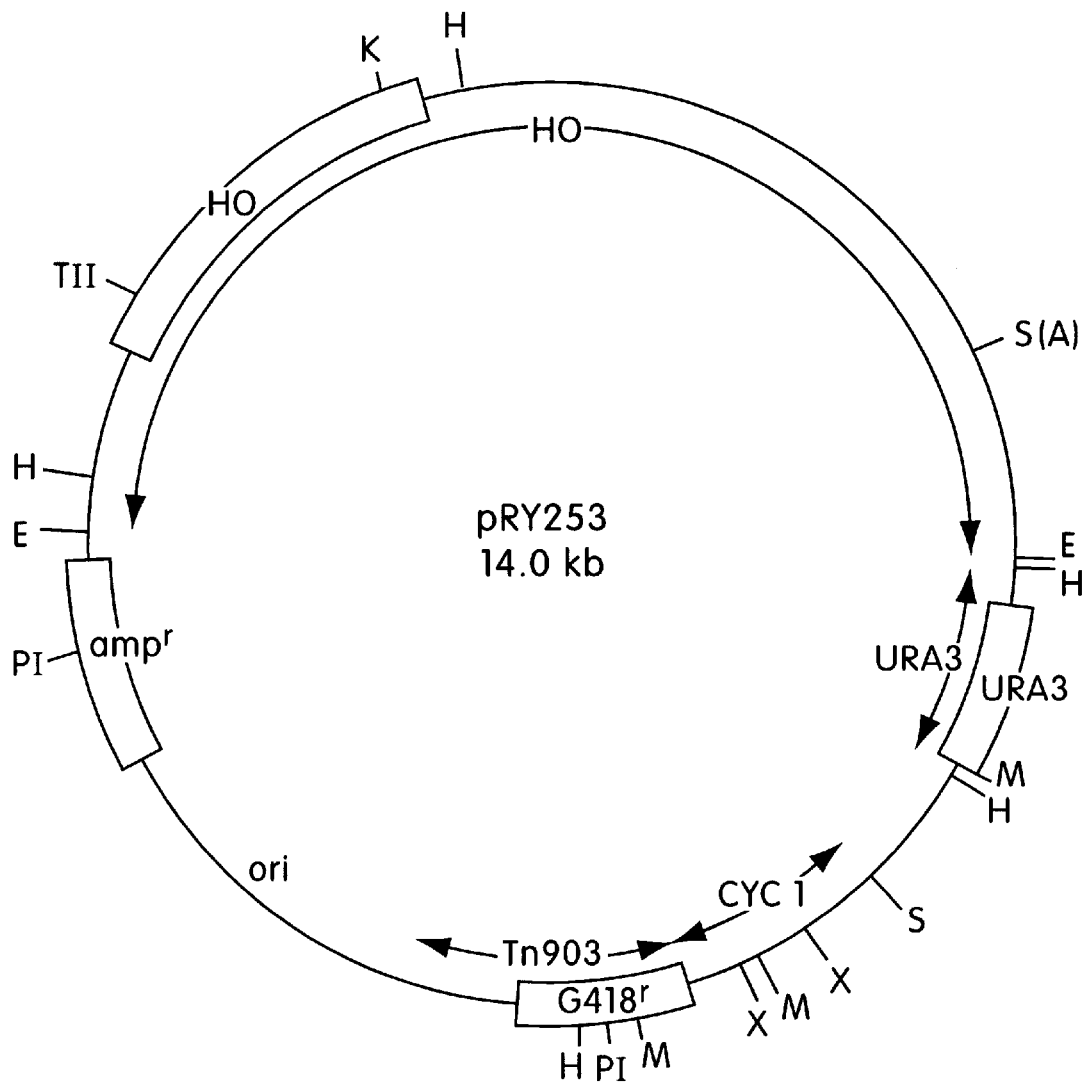
FIGS. 7 and 8 are diagrammatic representations of integrating vectors of the invention.

Referring to FIG. 7, integrating plasmid vector pRY253 is derived from pRY252 in that the yeast origin of replication sequence is replaced by a 7.0 kb EcoRI fragment of *S. cerevisiae* containing the Ho (homothallism) gene, including site K for insertion of a desired heterologous gene.

Figure 8:
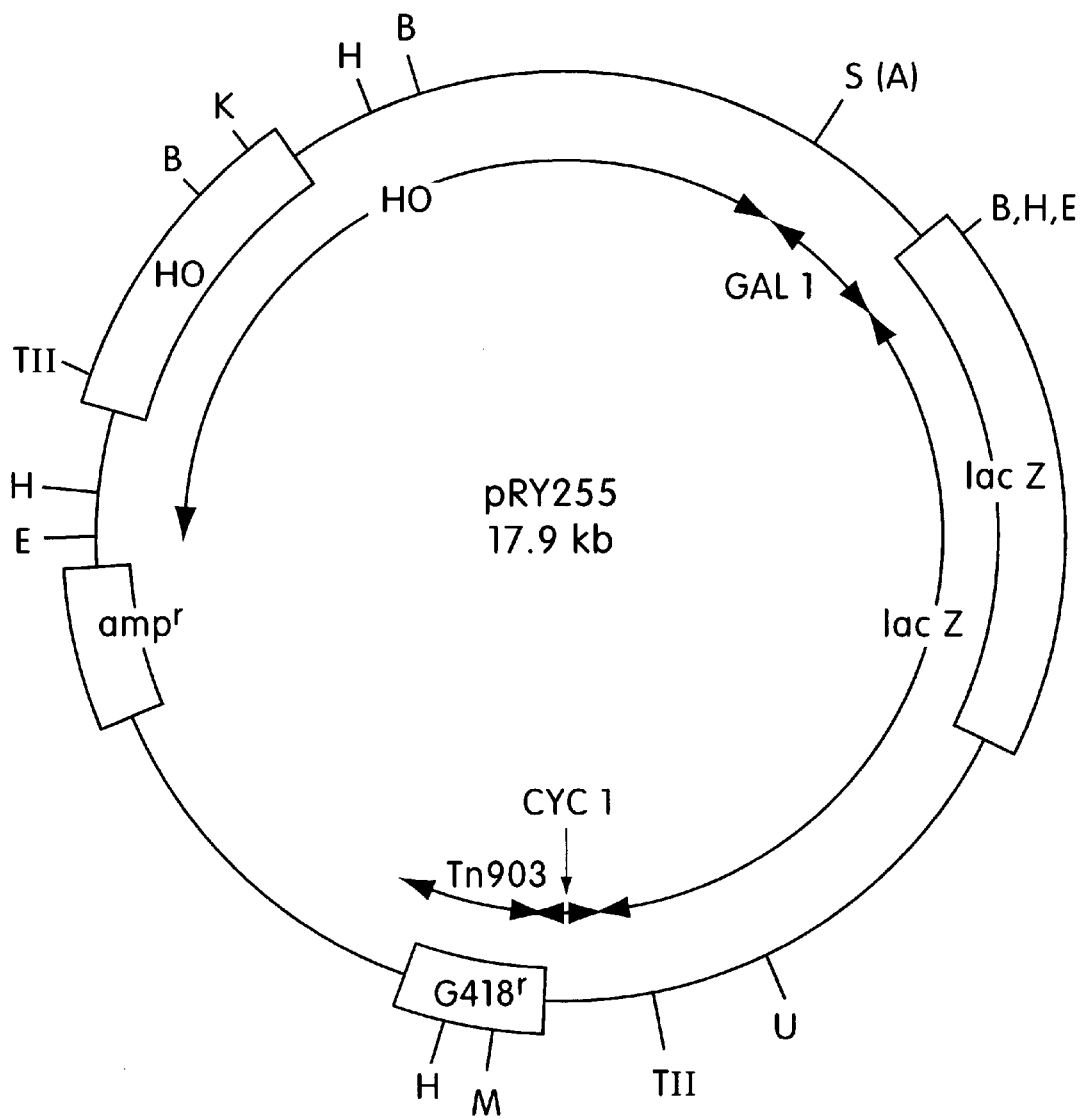

Referring to FIG. 8, integrating plasmid vector pRY255 is derived from pRY253 in that a 3.3 kilobase SalI to XhoI fragment extending from one end of the HO insert to the beginning of the CYC1 promoter sequence and containing the URA3 gene has been replaced with a 6.0 kilobase XhoI to SalI fragment containing a gene fusion of the yeast GAL1 gene and the *E. coli* lacZ gene. Referring to FIG. 1, pRY255A is similar to pRY255, in that it is also derived from pRY253, in that the 6.0 kilobase XhoI to SalI fragment containing the GAL1-lacZ fusion is substituted for the 2.5 kilobase SalI fragment of pRY253.

The plasmids illustrated in FIGS. 1 and 6–8 were made using conventional recombinant DNA methods and publicly available materials.

Plasmids pRY253, pRY255 and pRY255A were derived from replicating plasmid pRY252 which, briefly, was constructed as follows.

The URA3 gene was inserted into plasmid pBR322 as illustrated, and then the origin of replication from the endogenous yeast 2 micron circle, without the three genes normally accompanying it, was inserted. The vector is able to replicate in host yeast cells without containing these three genes, two of which encode proteins essential for replication, because host yeast cells already contain the endogenous 2 micron circle encoding those proteins (Botstein et al. (1979) Gene 8, 17).

The CYC1-G418$^r$ fusion portion of the plasmid was constructed by fusing the XhoI site near the 5' end of the G418$^r$ gene of transposon Tn903 (described in Oka et al. (1981) J. Mol. Biol. 147, 217) to the BamHI site following the CYC1 promoter and the 5' end of the CYC1 coding sequences of plasmid pLG669 (described in Guarente et al. (1981) PNAS USA 78, 2199) after rendering both ends flush with mung bean nuclease. The DNA sequence of this fusion junction is (CYC1) . . . TAAATTAATAATGACCGGGCC-G . . . (G418$^r$). The arrow shows the point of fusion.

Plasmids pRY253, pRY255 and pRY255A were constructed from pRY252 by making the gene fragment substitutions and deletions shown in the Figures.

The vectors of the invention can be used in any useful process in which host yeast cells express a desired heterologous gene. The desired heterologous gene can be inserted using conventional recombinant DNA techniques, e.g., as described in Maniatis et al. (1982) *Molecular Cloning: A Laboratory Manual*, Cold Spring Harbor Press, Cold Spring Harbor, N.Y., hereby incorporated by reference.

Vector Construction

The first step was the construction of pDY3 as described in Yocum, id. The next step was the isolation of the *A. niger* preglucoamylase gene.

Isolation of the *A. niger* Preglucoamylase Gene

*A. niger* was grown by shaking $10^6$ spores per liter at 30° C. in a medium containing, per liter, 7 g Yeast Nitrogen Base (Difco) and 20 g Soluble Starch (Fisher). Mycelium was harvested by filtration after 3 days of growth and total RNA was prepared by the method of Lucas et al. (1977) J. Bacteriol. 130, 1192.

PolyA-containing mRNA was isolated by two passes over oligo-dT-cellulose and used to construct a cDNA library by the standard method of G-C tailing into the PstI site of pBR322 (Maniatis et al. (1982) *Molecular Cloning,* Cold Spring Harbor Laboratory Press, Cold Spring Harbor, N.Y.). The cDNA library was transformed into *E. coli* strain YMC9. Single colonies from about 25,000 transformants were screened with a $^{32}$P-labeled synthetic 27 base oligonucleotide probe corresponding to amino acids 259–268 of *A. niger* glucoamylase as published by Svenson et al. (1983) Carlsberg Res. Commun. 48, 529. The sequence of the 27-mer was:

5'-GCATGCGACGACTCCACCTTCCAGCCC-3'

Twelve clones that hybridized with the probe were characterized. One of them, designated p1-19A, contained a 2,200 base pair insert that was shown by DNA sequence analysis to contain the entire coding sequence for preglucoamylase I, as described by Boel et al. (1984) EMBO J. 3, 1097.

Figure 3:
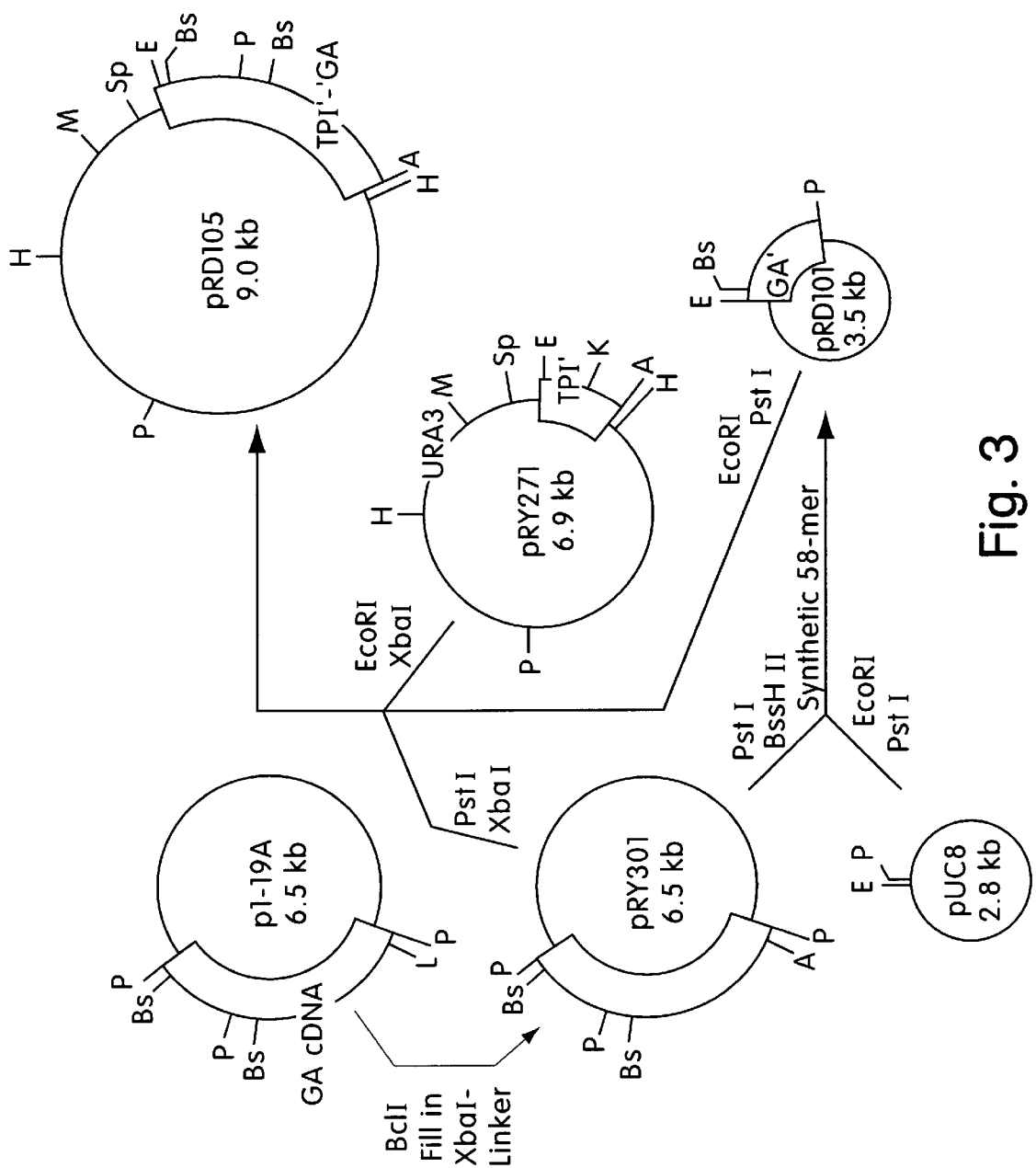

The following constructions and steps are illustrated in FIG. 3.

A unique BclI restriction site was located 54 base pairs downstream from the terminaton codon of the preglucoamylase I gene in p1-19A. This site was converted into an XbaI site by standard methods (Maniatis et al. (1982), id) to yield plasmid pRY301.

Figures 4, 5:
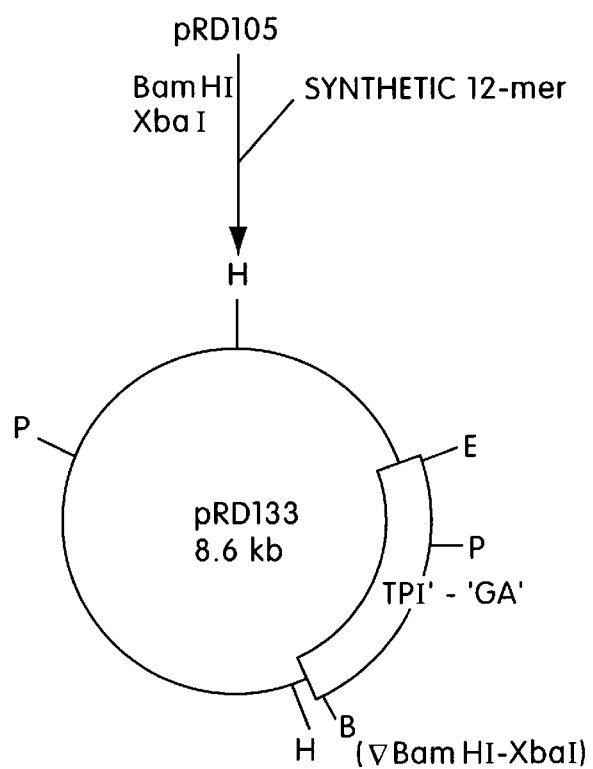
FIG. 4 is the nucleotide sequence of a 58-base segment of synthetic DNA used in the construction of said plasmid.

A BssHII to PstI fragment containing bases 69–746 of the preglucoamylase I coding sequence was cut out of pRY301 and ligated together with a synthetic 58-mer that replaces sequences lost in the subcloning of the BssHII to PstI fragment (FIG. 4) into the EcoRI to PstI backbone of pUC8 (New England Biolabs) to give pRD101.

Construction of Glucoamylase Fusion Gene

Preglucoamylase was expressed as a fusion protein from the *S. cerevisiae* TPI promoter. The gene coding for the fusion protein contains DNA including the TPI promoter, the first three amino acids of TPI, an EcoRI linker which creates an isoleucine codon, and preglucoamylase I beginning at the leucine at the sixth position. The DNA sequence around the fusion junction is:

Met Ala Arg Ile Leu Leu

ATG GCT AGA ATT CTA CTC

TAC CGA TCT TAA GAT GAG

The staggered line indicates the EcoRI cleavage site at the fusion junction. The gene fusion was constructed as follows.

pRY271 is an expression vector containing an EcoRI linker inserted at codon three of TPI and a natural XbaI site just upstream from the TPI transcription terminator (FIG. 3). Between the aforementioned EcoRI and XbaI sites was inserted two DNA fragments, the EcoRI-PstI piece of preglucoamylase cDNA from pRD101, and the PstI-XbaI piece of preglucoamylase cDNA from pRY301. This yielded pRD105.

The entire gene fusion from pRD105, containing the TPI promoter and terminator, and the TPI-preglucoamylase gene fusion on a SmaI-HindIII fragment, was then transferred by blunt end ligation with XhoI linkers into the KpnI site of pDY3 (FIG. 1), to yield the integrating plasmid pRD111 (FIG. 2).

An additional plasmid, pRD133 (FIG. 5), was constructed which contained a cDNA encoding a protein which mimics GII, described above; construction was as follows. Plasmid pRD105 was cut with BamHI and XbaI to remove the 3' end of the glucoamylase gene. The resulting fragment was ligated with a synthetic linker of the following sequence:

5'-GATCCTAGTAAC

GATCATTGGATC-5', to yield pRD133. Plasmid pRD133 was designed to encode a protein that is missing the amino acids covering the fifth intron, as well as a several additional amino acids on both sides of the intron. The linker was designed such that no extraneous amino acid sequences were introduced.

Upon transformation into yeast, pRD133 yields a slight increase (about 10%) in glucoamylase activity over pRD105, so yeast strains containing the shortened version of the glucoamylase gene may be preferred in some instances. The shortened version can be easily transferred to the integrating vector pDY3 on a SmaI to HindIII fragment, in a manner analogous to the construction of pRD111 from pRD105 as described above.

An integrating vector containing the shortened version of the glucoamylase gene can also be constructed from pRD111 as follows. pRD111 can be partially cleaved with BamHI under conditions that give an average of one BamHI cut per molecule. Full length linear plasmid can then be separated from circular (uncut) plasmid by standard preparative gel electrophoresis. The isolated linear plasmid can then be cleaved with XbaI and ligated with the synthetic linker described above.

Transformation of Polyploid Brewing Strains

American lager beer strains are more difficult to transform than most other yeast strains. In fact, we found it impossible to transform American lager strains with integrating plasmids using standard procedures such as is described in Webster et al. (1983) Gene 26, 243. Therefore, we devised a new method that is more efficient than standard procedures and that routinely allows transformation of American lager strains with integrating plasmids such as pRD111. The new method, which involves, as have previous methods, the use of antibiotic resistance to select transformants, avoids exposing the yeast cells to heated, molten agar, which we have found kills many or all of the cells. Instead, we expose the cells to the antibiotic by plating the cells on a porous support, e.g., filter paper, which is placed on top of solid, cool medium containing antibiotic, which contacts the cells after diffusing up through the porous support. The use of antibiotic resistance in an integrating vector permits selection of stable transformants in a yeast strain, regardless of the number of chromosomes or the presence or absence of specific mutations. In more detail, the method is as follows.

Lager strains were isolated from kegs of unpasteurized beer, e.g., Budweiser, by filtration of 500 ml beer through a 0.45 micron Nalgene disposable filter unit. The filter was excised with a sterile scalpel and placed on a petri plate of YEP-D agar (1% Difco Yeast Extract, 2% Difco Bacto-Peptone, 2% dextrose, and 2% agar) containing 20 ug/ml tetracycline and 100 ug/ml ampicillin. Yeast colonies appeared in three days. The yeast strain was identified as a close relative of *Saccharomyces cervisiae* by DNA hybridization of 2 micron DNA and HO DNA.

For transformation, the lager strains are typically grown to $2 \times 10^7$ cells/ml in YEP-D liquid medium. $4 \times 10^9$ cells are pelleted by centrifugation (all centrifugations are 5,000 rpm for 5 minutes) and rinsed once in 20 ml LTE (0.1M lithium acetate, 0.01M Tris-HCl, pH 7.4, 0.001M $Na_2$ EDTA). The cells are then resuspended in 20 ml LTE and incubated for 30 minutes at 30° C. on a roller drum. Cells are then pelleted, resuspended in 2.0 ml LTE, and aliquoted into 0.2 ml portions. 25 ug of plasmid DNA linearized at a site in the target sequence (for example, the unique SstII site in HO in the case of pRD111) is mixed with 25 ug of sheared calf thymus DNA in a total volume of 25 to 50 ul LTE and added to a 0.2 ml aliquot of treated cells. The mix of DNA and cells is kept on ice for 10 minutes and then is heat shocked in a 38° C. water bath for 5 minutes. After 10 more minutes on ice, 1.0 ml of 40% Polyethyleneglycol 4000 in LTE is mixed with the cell suspension. After 30 minutes on ice, the cells are pelleted and resuspended in 0.2 ml YEP-D. 0.1 ml of this suspension is spread on a Millipore filter (catalog number HATF 082 25) that has been placed flat on the surface of a YEP-D agar 0.1M $KPO_4$, pH 7.0 petri plate. After incubation at 300 for 2 generations (6–8 hours for American lager strains), the filter containing the yeast cells is transferred to a fresh petri plate of YEP-D agar 0.1M $KPO_4$, pH 7.0 plus 200–1000 ug/ml antibiotic G418. Care is taken to avoid bubbles of air between the agar and filters. Transformants appear out the background of untransformed cells as colonies after 3 or 4 days at 30° C. This procedure typically gives about 25–50 transformants per 25 ug of linearized integrating plasmid. The integrated state of the plasmid is routinely confirmed by Southern Blot analysis.

Jettisonning of Vector Sequences

A transformant containing pRD111 integrated at the HO locus is grown for 20–40 generations non-selectively in YEP-D liquid medium and plated at about 500 cells per petri plate on YEP-Gal-XG-BU agar (1% yeast extract, 2% peptone, 2% galactose, 0.006% 5'-bromo-4'-cloro-3'-indoyl-Beta-D-galactoside, 0.1M $KPO_4$, pH 7.0, 2% agar). After 5 days at 30° C., most colonies turn blue. Rare white colonies are picked onto MS agar (0.7% Difco Yeast Nitrogen Base, 2% Fisher soluble starch, 2% agar) to check for growth on starch as a sole carbon source. About one in $10^3$ to $10^4$ colonies are white, and about one in two of the white colonies secrete glucoamylase as evidenced by growth on starch. Confirmation of glucoamylase secretion is routinely checked by Western Blotting and identification of glucoamylase with a rabbit antibody to purified *A. niger* glucoamylase.

Once the gene encoding glucoamylase has been integrated and the unwanted sequences jettisonned, the above-described procedure may be repeated, to integrate additional copies of the gene into other chromosomes, or other locations within a chromosome. This can result, e.g., in the integration of the gene into every chromosome of a host yeast cell having the homologous target region. Creating multiple copies of the gene yields these advantages: 1)

increased expression of the gene; 2) increased stability of the resulting strains, perhaps by decreasing the probability of gene conversion which could result in the loss of the gene.

Brewing Strains

A single copy of the TPI-glucoamylase fusion was deposited in one copy of the HO gene of an American lager brewing strain, Brew 1, as described above. The vector sequences were jettisoned and the final structure of the deposited gene was confirmed by Southern Blots. This new strain is called Brew 1/pRD111-R (the R stands for Revertant).

Two batches of beer were simultaneously brewed from the same lot of wort, one batch with Brew 1/pRD111-R and the other with untransformed Brew 1. The wort contained, per liter, 150 grams of Munton and Fison Amber Malt Extract, 0.5 gram Hallertau Hops Pellets, 0.5 gram Burton Water Salts, and 2.0 grams of Yeast Nutrient Salts (Beer and Wine Hobby, Greenwood, Mass. 01880). A 5% innoculum was grown aerobically to saturation in wort and then added to an anaerobic fermentor. After 9 days of fermentation at 15° C., the raw beer was tranferred to a clean fermenter, leaving behind the bulk of the settled yeast, after which the beer was stored for 3 weeks at 15° C.

The fermented beer was then analyzed for the presence of dextrins. A 1 ml sample of beer was treated with 1 ul of a commercial preparation of *A. niger* glucoamylase (DIAZYME 200L$^R$, Miles Laboratories) for 3 hours at 50° C. These conditions had been shown to effect complete digestion of any residual dextrins to glucose. A 25 ul sample of each digest was then analyzed for glucose on a Yellow Springs Instruments Model 27 glucose analyzer. The beer brewed by the transformed strain, Brew 1/pRD111-R, contained substantially reduced levels of dextrin compared to the control beer brewed by untransformed Brew 1. High pressure liquid chromatography of the two beers, using a 10 cm Spheri 5 RC 8 column coupled to a 22 cm Polypore H column (both from Rainin Instruments) and 0.01N $H_2SO_4$ as the eluant, confirmed that residual dextrins were reduced by the engineered strain compared to the control strain.

Deposit

The following deposits have been made with the American Type Culture Collection (ATCC), where the deposits were given the following accession numbers:

| Deposit | Accession No. |
|---|---|
| pRY252 | ATCC 39687 |
| pRY253 | ATCC 39688 |
| pRY255 | ATCC 39689 |
| pRY255A | ATCC 39822 |
| pRD111 in *E. coli* YMC9 | ATCC 53123 |

Applicants' assignee, Robert R. Yocum, acknowledges its responsibility to replace these cultures should they die before the end of the term of a patents issued hereon, and its responsibility to notify the ATCC of the issuance of such a patent, at which time the deposit will be made available to the public. Until that time the deposit will be made available to the Commissioner of Patents under the terms of 37 CFR §1.14 and 35 §112.

OTHER EMBODIMENTS

For example, in addition to enzymes involved in the production of bread and alcoholic beverages, the vectors of the invention can be used in processes in which the desired end product is the protein, e.g., therapeutic proteins such as interferon, encoded by the inserted heterologous gene. The heterologous gene can also be a gene already carried on a different portion of the host chromosome; for example, it might be advantageous to add an additional copy of a native gene involved in alcohol production, to increase production levels.

The promoter sequence controlling the gene for antibiotic resistance can also vary widely, the only crucial factor being that the sequence provides that a sufficient level of expression in yeast cells is maintained.

Other embodiments are within the following claims. Additionally, as mentioned above, any suitable diploid or greater ploidy yeast can be used in the invention. Suitable strains include the ones listed below, all of which contain the HO gene, which facilitates integration.

| Strain Name | Species | Type |
|---|---|---|
| Budweiser | *S. uvarum* | lager |
| ATCC 42928 | *S. cerevisiae* | wine |
| Fleischman | *S. cerevisiae* | bread |
| Red Star | *S. cerevisiae* | bread |
| Red Star Quick Rise | *S. cerevisiae* | bread |
| 1354 | *S. diastaticus* | lab |
| DBY 745 | *S. cerevisiae* | lab |
| DCL-M | *S. cerevisiae* | distillery |

"pRY253, pRY255, pRY255A, and pDY3 can also be used to delete genes from wild type yeast strains. For the deletion of genes, the HO portion of the vectors becomes irrelevant. Deletion of a gene or a portion of a gene can be accomplished as follows:

1. Clone the gene to be deleted with some adjacent sequences on both sides of the gene.
2. Create a deletion of the cloned gene in vitro, leaving some adjacent sequences from both ends of the gene.
3. Place the deletion-containing DNA at an appropriate location in one of the integration vectors described herein.
4. Linearize the vector at a point in one of the sequences adjacent to the deletion, and perform integrative transformation, selecting for G418 antibiotic resistance.
5. Grow a stable transformant for 20 to 40 generations non-selectively, and screen for vector jettisoning events either by loss of blue colony color on Xgal (see below) indicator plates, or by replica plating to G418-containing plates.
6. Screen among colonies that have jettisoned the vector for those that retained the deleted version of the gene by Southern blotting."

What is claimed is:

1. An isolated DNA sequence comprising:
   a) a gene encoding resistance to an antibiotic, wherein said antibiotic inhibits growth of an untransformed host yeast cell,
   b) a promotor sequence that is not naturally associated with said gene encoding antibiotic resistance, wherein said antibiotic resistance gene is transcribed from said promotor sequence, such that said DNA sequence provides for direct selection for said DNA sequence upon transformation into said host yeast cell, wherein the first selective medium encountered by the transformed cells subsequent to transformation contains said antibiotic, and wherein said promotor sequence is capable of transcribing said antibiotic resistant gene such that said isolated DNA provides for said direct selection upon integration of said DNA sequence into a chromosome of said host yeast cell, and c) a DNA sequence that is homologous to a portion of a chromosome of said host yeast cell.

2. The DNA sequence of claim 1 wherein said gene encodes resistance to antibiotic G418.

3. The DNA sequence of claim 1 or claim 2 wherein said promoter sequence is substantially identical to the promoter sequence of the yeast CYC1 (cytochrome c) gene.

4. A vector comprising the DNA sequence of claim 1.

5. The DNA of claim 1, said DNA further comprising a second gene that is heterologous to said host yeast.

6. A yeast cell transformed with the vector of claim 4 or the DNA of claim 1 or 5 or a descendant of said transformed yeast cell.

7. A method for producing a desired protein encoded by a heterologous gene comprising culturing a transformed yeast of claim 6 under conditions that result in the production of said protein.

8. A yeast cell transformed with the DNA of claim 1 or the vector of claim 4, or a descendant of said transformed yeast cell.

9. A method of transforming a host yeast cell, comprising:
a) exposing a population of host yeast cells, that are sensitive to an antibiotic, to the DNA of any of claims 1, 4, or 5 under transforming conditions,
b) applying said antibiotic at a concentration sufficient to inhibit growth of untransformed cells, wherein the first selective medium encountered by the transformed cell subsequent to transformation contains said antiobiotic; and
c) selecting cells that grow in the presence of said antibiotic.

10. The vector pRY253, shown in FIG. 7.

11. The vector pRY255, shown in FIG. 8.

12. The vector pRY255A.

* * * * *